United States Patent
Stockton (12) 
(10) Patent No.: US 6,653,082 B2
(45) Date of Patent: Nov. 25, 2003

(54) SUBSTRATE-BOUND CLEAVAGE ASSAY FOR NUCLEIC ACID ANALYSIS

(75) Inventor: David W. Stockton, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 10/150,051

(22) Filed: May 16, 2002

(65) Prior Publication Data

US 2002/0187505 A1 Dec. 12, 2002

Related U.S. Application Data (60) Provisional application No. 60/291,587, filed on May 17, 2001.

(51) Int. Cl.$^7$ .................................. C12Q 1/68
(52) U.S. Cl. ........................................ 435/6
(58) Field of Search ................ 435/6, 5, 34, 172.1, 435/172.3, 820, 91.2, 91.1, 91.52; 436/501, 94; 536/24.31, 24.32, 24.3

(56) References Cited

U.S. PATENT DOCUMENTS

| | | | |
|---|---|---|---|
| 4,689,405 A | | 8/1987 | Frank et al. |
| 5,002,867 A | | 3/1991 | Macevicz |
| 5,202,231 A | | 4/1993 | Drmanac et al. |
| 5,364,759 A | | 11/1994 | Caskey et al. |
| 5,470,710 A | | 11/1995 | Weiss et al. |
| 5,674,686 A | | 10/1997 | Schumm et al. |
| 6,403,309 B1 | * | 6/2002 | Iris et al. ........................ 435/6 |

FOREIGN PATENT DOCUMENTS

| | | |
|---|---|---|
| WO | WO 89/10977 | 11/1989 |
| WO | WO 90/13666 | 11/1990 |
| WO | WO 91/06678 | 5/1991 |
| WO | WO 92/15712 | 9/1992 |
| WO | WO 93/05183 | 3/1993 |
| WO | WO 93/13220 | 7/1993 |
| WO | WO 93/15228 | 8/1993 |
| WO | WO 93/17126 | 9/1993 |
| WO | WO 95/00669 | 1/1995 |

OTHER PUBLICATIONS

Gingeras, T.R., et al., "Hybridization properties of immobilized nucleic acids," *Nucleic Acids Research* 15(13):5373–5391 (1987).

Guo, Z., et al., "Direct fluorescence analysis of genetic polymorphisms by hybridization with oligonucleotide arrays on glass supports," *Nucleic Acids Research* 22(24):5456–5465 (1994).

* cited by examiner

Primary Examiner—Kenneth R. Horlick
(74) Attorney, Agent, or Firm—Hamilton, Brook, Smith & Reynolds, P.C.

(57) ABSTRACT

Assays for analyzing a sample comprising nucleic acid are described, in which the sample is contacted with an array comprising a set of oligonucleotides attached to a solid support at identifiable locations, wherein each oligonucleotide in the set comprises a label at the distal end of the oligonucleotide; incubating the contacted array to allow hybridization of nucleic acid in the sample to the oligonucleotides of the array; subjecting the hybridized array to a cleavage agent which cleaves incompletely hybridized oligonucleotides but does not cleave completely hybridized oligonucleotides; washing the cleaved array; and assessing a pattern of negative and positive signals on the washed, cleaved array, wherein a negative signal corresponds to an incompletely hybridized oligonucleotide that was cleaved by the cleavage agent, thus removing the label, and a positive signal corresponds to an oligonucleotide that was not cleaved by the cleavage agent, thus retaining the label.

34 Claims, 3 Drawing Sheets

|  |  |  |  |
|---|---|---|---|
| Phe508Del | A | ccattaaagaaaatatcatctttggtgttttcctatgatgaata | (SEQ ID NO:1) |
|  | B | ccattaaagaaaatatcatc....ggtgttttcctatgatgaata | (SEQ ID NO:2) |
| Ile507Del | C | gcaccattaaagaaaatatcatctttggtgttttcctatgatga | (SEQ ID NO:3) |
|  | D | gcaccattaaagaaaatatc....tttggtgttttcctatgatga | (SEQ ID NO:4) |
| Asp110His | E | gaagaatcatagcttcctatgacccgataacaaggaggaa | (SEQ ID NO:5) |
|  | F | gaagaatcatagcttcctatcacccgataacaaggaggaa | (SEQ ID NO:6) |
| Gln493Ter | G | gaagaatttcattctgttctcagtttttcctggattatgcc | (SEQ ID NO:7) |
|  | H | gaagaatttcattctgttcttagtttttcctggattatgcc | (SEQ ID NO:8) |
| 2566insAT | I | ccttcgatatattactgtcc...acaagagcttaattttttgtgct | (SEQ ID NO:9) |
|  | J | ccttcgatatattactgtccatacaagagcttaattttttgtgct | (SEQ ID NO:10) |
| 3659delC | K | gccctcaggggccaaatgactgtcaaagatctcacagcaa | (SEQ ID NO:11) |
|  | L | gccctcaggggccaaatga.tgtcaaagatctcacagcaa | (SEQ ID NO:12) |

SEQUENCE LISTING

<160> NUMBER OF SEQ ID NOS: 12

<210> SEQ ID NO 1
<211> LENGTH: 43
<212> TYPE: DNA
<213> ORGANISM: Homo sapiens

<400> SEQUENCE: 1
ccattaaaga aaatatcatc tttggtgttt cctatgatga ata          43

<210> SEQ ID NO 2
<211> LENGTH: 40
<212> TYPE: DNA
<213> ORGANISM: Homo sapiens

-continued

```
<400> SEQUENCE: 2
ccattaaaga aaatatcatc ggtgtttcct atgatgaata                              40

<210> SEQ ID NO 3
<211> LENGTH: 43
<212> TYPE: DNA
<213> ORGANISM: Homo sapiens

<400> SEQUENCE: 3
gcaccattaa agaaaatatc atctttggtg tttcctatga tga                         43

<210> SEQ ID NO 4
<211> LENGTH: 40
<212> TYPE: DNA
<213> ORGANISM: Homo sapiens

<400> SEQUENCE: 4
gcaccattaa agaaaatatc tttggtgttt cctatgatga                             40

<210> SEQ ID NO 5
<211> LENGTH: 41
<212> TYPE: DNA
<213> ORGANISM: Homo sapiens

<400> SEQUENCE: 5
gaagaatcat agcttcctat gacccggata acaaggagga a                           41

<210> SEQ ID NO 6
<211> LENGTH: 41
<212> TYPE: DNA
<213> ORGANISM: Homo sapiens

<400> SEQUENCE: 6
gaagaatcat agcttcctat cacccggata acaaggagga a                           41

<210> SEQ ID NO 7
<211> LENGTH: 40
<212> TYPE: DNA
<213> ORGANISM: Homo sapiens

<400> SEQUENCE: 7
gaagaatttc attctgttct cagttttcct ggattatgcc                             40

<210> SEQ ID NO 8
<211> LENGTH: 40
<212> TYPE: DNA
<213> ORGANISM: Homo sapiens

<400> SEQUENCE: 8
gaagaatttc attctgttct tagttttcct ggattatgcc                             40

<210> SEQ ID NO 9
<211> LENGTH: 42
<212> TYPE: DNA
<213> ORGANISM: Homo sapiens

<400> SEQUENCE: 9
ccttcgatat attactgtcc acaagagctt aattttgtg ct                           42

<210> SEQ ID NO 10
<211> LENGTH: 44
<212> TYPE: DNA
<213> ORGANISM: Homo sapiens
```

```
<400> SEQUENCE: 10
ccttcgatat attactgtcc atacaagagc ttaatttttg tgct                              44

<210> SEQ ID NO 11
<211> LENGTH: 41
<212> TYPE: DNA
<213> ORGANISM: Homo sapiens

<400> SEQUENCE: 11
gccctcaggg ggccaaatga ctgtcaaaga tctcacagca a                                 41

<210> SEQ ID NO 12
<211> LENGTH: 40
<212> TYPE: DNA
<213> ORGANISM: Homo sapiens

<400> SEQUENCE: 12
gccctcaggg ggccaaatga tgtcaaagat ctcacagcaa                                   40
```

SUBSTRATE-BOUND CLEAVAGE ASSAY FOR NUCLEIC ACID ANALYSIS

RELATED APPLICATION

This application claims the benefit of U.S. Provisional Application No. 60/291,587, filed on May 17, 2001, the entire teachings of which are incorporated herein by reference.

BACKGROUND OF THE INVENTION

Analysis of nucleic acid sequences is being used more and more frequently to determine the "genotype," or specific type of a particular genetic element, for a nucleic acid sample. Because variant genetic elements exist, techniques have been developed to compare homologous nucleic acids to determine if they are identical, or if they differ by one or more nucleotides. The available genotyping techniques have disadvantages that limit their widespread use and/or efficacy. For example, restriction fragment length polymorphism (RFLP)-based analysis requires large amounts of sample DNA, and has a low density of mapped polymorphisms; furthermore, the number of alleles at each locus is small, leading to a low heterozygosity and therefore an inability to differentiate or distinguish between the homologous nucleic acids a high percentage of the time (Southern, E. M., *J Mol. Biol.* 98:503–517 (1975); Botstein, D. et al., *Am. J Hum. Gen.* 32:314–331 (1980)). Short sequence repeat (SSR)-based analysis, which typically utilizes polymerase chain reaction (PCR), reduces the amount of DNA required in comparison with RFLP analysis; furthermore, there are usually many different alleles at each locus leading to high heterozygosity and thus more informative analyses (Miesfeld. R. et al, *Nucl. Acids Res.* 9:5931–5947 (1987); Weber, J. L., *Genomics* 7:524–530 (1990)). However, SSR analysis is traditionally a gel-based technique, and is therefore a slow and labor-intensive method: running and reading of gels is expensive, time consuming, error prone and difficult to automate. Because these techniques are being used in an increasing number of fields, such as genetic disease diagnosis, infectious disease diagnosis, forensic identification, paternity determination, and genetic disease or locus mapping, a need exists for simple and efficient methods of genotyping and genetic analysis.

SUMMARY OF THE INVENTION

The present invention pertains to assays for analyzing a sample comprising a nucleic acid of interest. In the assays, an array comprising a set of oligonucleotides attached to a solid support is used. Each oligonucleotide in the set comprises a first boundary sequence, a second boundary sequence, a nucleic acid marker, and a label. The first boundary sequence is at the proximal end of the oligonucleotide, relative to the solid support to which the oligonucleotide is attached; the second boundary sequence and the label are at the distal end of the oligonucleotide, relative to the solid support to which the oligonucleotide is attached; and the nucleic acid marker is between the first and the second boundary sequence. The boundary sequences are invariant, and the nucleic acid marker includes the polymorphic region to be assayed.

In one embodiment, the nucleic acid marker is a number N of consecutive repeats of a nucleic acid sequence element. In this embodiment, each nucleic acid marker in the set of oligonucleotides has a different number of consecutive repeats of the nucleic acid sequence element, the number ranging from N to N+A, inclusive. The minimum number N of repeats is generally between 0–40 repeats; the range number (A) is generally between 3 and 20. In another embodiment, the nucleic acid marker contains a single nucleotide polymorphism; each nucleic acid marker in the set of oligonucleotides has a nucleic acid marker that contains a different nucleotide at a polymorphic nucleotide site. In a third embodiment, the nucleic acid marker contains allele-specific polymorphisms; each nucleic acid marker in the set of oligonucleotides contains a different historically observed allele-specific polymorphism. In a fourth embodiment, the nucleic acid marker contains a fragment of the nucleic acid of interest; each nucleic acid marker in the set of oligonucleotides has a different fragment of the nucleic acid of interest, such that the entire nucleic acid of interest is represented by the nucleic acid markers in the set of oligonucleotides.

In the assays, the oligonucleotides are attached to a solid support at identifiable locations, forming the array. The set of oligonucleotides is attached such that the composition and position of each oligonucleotide on the array is identifiable. The array is contacted with a test sample that contains the nucleic acid of interest, or that is to be assessed for the presence of the nucleic acid of interest, and is maintained under conditions which allow hybridization of nucleic acid in the test sample to the oligonucleotides of the array. The array is then exposed to a cleavage agent (single strand or double strand) which cleaves oligonucleotides that are imperfectly hybridized (i.e., not complementary at every location along their sequence) to nucleic acid in the test sample, but does not cleave oligonucleotides that are perfectly hybridized (i.e., that are completely complementary) to nucleic acid in the test sample. The array is then washed to remove any cleavage products, and the pattern of negative and positive signals on the washed, cleaved array is observed. A negative signal corresponds to an imperfectly hybridized oligonucleotide that was cleaved by the cleavage agent (thus removing the label), and a positive signal corresponds to an oligonucleotide that was not cleaved by the cleavage agent.

The assays of the invention allow fully automated high density array or chip-based analysis with a variety of nucleic acid markers, including nucleic acid sequence elements derived from highly polymorphic short sequence repeat markers and markers forming a high density of polymorphisms, such as single nucleotide polymorphisms. The assays allow quick, highly informative assessment of genetic polymorphisms and alterations, thereby facilitating analysis and/or genotyping of a nucleic acid sample. If the genetic polymorphism is an allele-specific polymorphism representing disease-associated alterations, then the assay allows quick, highly informative assessment of disease gene status. The assay also allows quick, highly informative assessment of nucleic acids for the presence of any previous known or unknown alterations in sequence.

DETAILED DESCRIPTION OF THE INVENTION

The present invention relates to assays for analyzing a test sample comprising nucleic acid, and particularly for genotyping a nucleic acid of interest, that identify observable genetic polymorphisms and/or alterations (either previously identified, or previously unidentified (unknown)) in a nucleic acid of interest. As used herein, a "test sample" refers to a sample that contains nucleic acid, such as a nucleic acid of interest, or to a sample that is to be assessed for the presence of a nucleic acid of interest. A "nucleic acid of interest" refers to a particular nucleic acid for which analysis or genotyping is desired. Representative nucleic acids of interest include DNA or DNA fragments, including genes or gene fragments; or RNA or RNA fragments. In one embodiment, the nucleic acid of interest is genomic DNA comprising part of the genome of an individual or groups of individuals, such as one or more chromosome(s) or PCR products; in another embodiment, the nucleic acid of interest is genomic DNA comprising the entire genome of an individual or a group of individuals. The nucleic acid of interest can be single- or double-stranded. The test sample can comprise nucleic acid (which may or may not comprise the nucleic acid of interest) that is isolated; that is, the nucleic acid in the test sample is separated from the environment in which it is usually found. Alternatively, the test sample can be a biological sample. Representative biological samples include tissues, organs, or bodily fluids (e.g., blood, urine, tears, or any bodily secretions).

The genetic polymorphisms and alterations that can be identified by the methods of the invention include, but are not limited to, short sequence repeat (SSR) polymorphisms; variable number of tandem repeat (VNTR) polymorphisms; single nucleotide polymorphisms (SNPs); allele-specific polymorphisms; and microdeletions.

Short Sequence Repeat Polymorphisms

Short sequence repeat (SSR) polymorphisms (also known as "short tandem repeat" or "simple sequence repeat" polymorphisms, or "microsatellites" or "microsatellite repeats") are present in many loci in the human genome (see, for example, Edwards et al. *Am. J Hum. Genet.* 49(4) :746–756 (1991)), Beckman and Weber, *Genomics* 12:627–631 (1992)). Many different alleles are usually present at each SSR locus (Weber, J. L., *Genomics* 7:524–530 (1990)), leading to high heterozygosities. The high probability of heterozygosity provides more useful information from a finite set of samples in a given population.

A short sequence repeat (SSR) locus in a nucleic acid sample consists of a series of repeats of a short nucleic acid sequence element. A "nucleic acid sequence element," as used herein, is a short series of consecutive nucleic acids. Generally, a nucleic acid sequence element in an SSR locus is from 2 to 10 bases in length, although a nucleic acid sequence element can also be a single base, repeated. The bases of nucleic acid sequence elements found in nature can be part of base pairs (e.g., are double-stranded nucleic acids); the term "nucleic acid sequence element" refers to one strand (a "first" strand) of such base pairs.

Representative 2-base nucleic acid elements include the following elements: AC, AG, AT, CG, CT, and GT. The two bases can be in the order set forth, or in the reverse order. Representative 3-base nucleic acid elements include the following elements (the three bases can be in any order in a nucleic acid sequence element, and are not limited to the order set forth): TTT, TTC, TTA, TTG, TCT, TCC, TCA, TCG, TAT, TAC, TAA, TAG, TGT, TGC, TGA, TGG, CTT, CTC, CTA, CTG, CCT, CCC, CCA, CCG, CAT, CAC, CAA, CAG, CGT, CGC, CGA, CGG, ATT, ATC, ATA, ATG, ACT, ACC, ACA, ACG, AAT, AAC, AAA, AAG, AGT, AGC, AGA, AGG, GTT, GTC, GTA, GTG, GCT, GCC, GCA, GCG, GAT, GAC, GAA, GAG, GGT, GGC, GGA, and GGG. Representative 4-base nucleic acid elements include the following elements (the four bases can be in any order in a nucleic acid sequence element, and are not limited to the order set forth): TTTA, TTCA, TTAA, TTGA, TCTA, TCCA, TCAA, TCGA, TATA, TACA, TAAA, TAGA, TGTA, TGCA, TGAA, TGGA, CTTA, CTCA, CTAA, CTGA, CCTA, CCCA, CCAA, CCGA, CATA, CACA, CAAA, CAGA, CGTA, CGCA, CGAA, CGGA, ATTA, ATCA, ATAA, ATGA, ACTA, ACCA, ACAA, ACGA, AATA, AACA, AAAA, AAGA, AGTA, AGCA, AGAA, AGGA, GTTA, GTCA, GTAA, GTGA, GCTA, GCCA, GCAA, GCGA, GATA, GACA, GAAA, GAGA, GGTA, GGCA, GGAA, GGGA, TTTC, TTCC, TTAC, TTGC, TCTC, TCCC, TCAC, TCGC, TATC, TACC, TAAC, TAGC, TGTC, TGCC, TGAC, TGGC, CTTC, CTCC, CTAC, CTGC, CCTC, CCCC, CCAC, CCGC, CATC, CACC, CAAC, CAGC, CGTC, CGCC, CGAC, CGGC, ATTC, ATCC, ATAC, ATGC, ACTC, ACCC, ACAC, ACGC, AATC, AACC, AAAC, AAGC, AGTC, AGCC, AGAC, AGGC, GTTC, GTCC, GTAC, GTGC, GCTC, GCCC, GCAC, GCGC, GATC, GACC, GAAC, GAGC, GGTC, GGCC, GGAC, GGGC, TTTT, TTCT, TTAT, TTGT, TCTT, TCCT, TCAT, TCGT, TATT, TACT, TAAT, TAGT, TGTT, TGCT, TGAT, TGGT, CTTT, CTCT, CTAT, CTGT, CCTT, CCCT, CCAT, CCGT, CATT, CACT, CAAT, CAGT, CGTT, CGCT, CGAT, CGGT, ATTT, ATCT, ATAT, ATGT, ACTT, ACCT, ACAT, ACGT, AATT, AACT, AAAT, AAGT, AGTT, AGCT, AGAT, AGGT, GTTT, GTCT, GTAT, GTGT, GCTT, GCCT, GCAT, GCGT, GATT, GACT, GAAT, GAGT, GGTT, GGCT, GGAT, GGGT, TTTG, TTCG, TTAG, TTGG, TCTG, TCCG, TCAG, TCGG, TATG, TACG, TAAG, TAGG, TGTG, TGCG, TGAG, TGGG, CTTG, CTCG, CTAG, CTGG, CCTG, CCCG, CCAG, CCGG, CATG, CACG, CAAG, CAGG, CGTG, CGCG, CGAG, CGGG, ATTG, ATCG, ATAG, ATGG, ACTG, ACCG, ACAG, ACGG, AATG, AACG, AAAG, AAGG, AGTG, AGCG, AGAG, AGGG, GTTG, GTCG, GTAG, GTGG, GCTG, GCCG, GCAG, GCGG, GATG, GACG, GAAG, GAGG, GGTG, GGCG, GGAG, and GGGG. An SSR locus generally contains a nucleic acid sequence element repeated multiple times in tandem. For example, for a repeat element of (CA), four tandem repeats would be (CACACACA). In one embodiment, the nucleic acid sequence element is repeated from about 10 to 60 times if the nucleic acid sequence element is 2 bases in length; a repeat length of 10 or more increases the likelihood of the presence of polymorphism in any given population. In another embodiment, the nucleic acid sequence element is repeated from about 5 to 40 times if the nucleic acid sequence element is 3 or more bases in length. Variation in the number of repeats of a nucleic acid sequence element in a particular SSR locus results in an observable polymorphism.

Variable Number of Tandem Repeat Polymorphisms

A variable number of tandem repeat (VNTR) polymorphism (also referred to as "minisatellites" or "minisatellite repeats") is similar to a short sequence repeat polymorphism, in that is refers to a series of repeats of a short nucleic acid sequence element. Generally, a nucleic acid sequence element in a VNTR locus is longer than a nucleic acid sequence element in an SSR locus, ranging from about 10 to 60 bases in length (Bell, G. I. et al., *Nature* 295:31–35 (1982); Ali, S. and Wallace, R. B., *Nucl. Acids Res.* 16:8487–8496 (1988)). A VNTR locus generally contains a nucleic acid sequence element repeated from about 5 to 40 times. Variation in the number of repeats of a nucleic acid sequence element in a particular VNTR locus results in an observable polymorphism.

Single Nucleotide Polymorphisms

A "single nucleotide polymorphism" refers to a single nucleotide, at a known location in a genome, that varies among different members a population. It is estimated that single nucleotide polymorphisms occur every 1,000 base pairs in the human genome (Wang, D. G. et al., *Science* 280:1077–1082 (1998)). The degree of polymorphism for single nucleotide polymorphisms is much lower than for short sequence repeats or VNTRs, because the number of different nucleotides that may be present at a polymorphism site is limited to four; however, the density of the polymorphisms is much higher, because of the frequency of the single nucleotide polymorphisms in the genome.

Allele-Specific Polymorphisms

An "allele-specific polymorphism" is an alteration (e.g., deletion, insertion and/or substitution of one or more nucleotides) in a particular nucleic acid, such as a nucleic acid containing a gene. If the allele-specific polymorphism is associated with a gene, one (or more) allele(s) may be associated with disease, and one is considered to be the "wild-type" (normal) allele. Allele-specific oligonucleotides are frequently used to identify the presence of a normal or disease allele (Conner, B. J. et al., *Proc. Natl. Acad. Sci.* 80:278–282 (1983)).

Microdeletions

The term "microdeletion" refers to a deletion of a fragment of nucleic acid; typically, though not always, a microdeletion is not visible with high resolution chromosome analysis or karyotyping. Microdeletions range from deletions of a small number of base pairs, up to millions of base pairs. Frequently, microdeletions are associated with a disease state (see, e.g., motor neuron disease in Comi, G. P. et al., *Ann. Neurol.* 43:110–116(1998); cystic fibrosis, Iannuzzi, M. C. et al., *Am. J Hum. Genet.* 48:2270231 (1991); see also, Schmickel, R. D., *J. Pediatrics* 109:231–241 (1986))).

Microinsertions

The term "microinsertion" refers to an insertion of a fragment of nucleic acid. Microinsertions range from insertions of a small number of base pairs, up to millions of base pairs. Microinsertions are commonly duplications of nucleic acids, either in tandem or inverted (see, e.g., cystic fibrosis, Iannuzzi, M. C. et al., *Am. J Hum. Genet.* 48:2270231 (1991); Down syndrome, Huret, J. L. et al., *Hum. Genet.* 75:251–257 (1987)).

Assays of the Invention

The assays of the invention take advantage of the above-described genetic polymorphisms or alterations in analyzing or genotyping a nucleic acid of interest. In the assays of the invention, the nucleic acid in a test sample is hybridized to an array comprising a set of single-stranded oligonucleotides. Each oligonucleotide in a set contains a first boundary sequence of nucleic acid, as well as a second boundary sequence of nucleic acid. The boundary sequences are nucleic acids of approximately 5 to 30 bases in length, preferably about 20 bases in length, and are designed such that they will hybridize to known nucleic acids, such as to the nucleic acid of interest. For example, the boundary sequences can comprise, or be similar to, polymerase chain reaction (PCR) primers for a region of nucleic acid that is of interest, with both primers hybridizing to the same nucleic acid strand. In another example, the boundary sequences can be nucleic acids that flank single nucleotide polymorphism or an allele-specific polymorphism. Nucleic acid "flanking" a polymorphic nucleotide in a single nucleotide polymorphism, an allele-specific polymorphism, refers to nucleic acid that is, in nature, contiguous with the nucleotide (s) that is polymorphic. The flanking nucleic acid that is included in the boundary sequences can be contiguous with the 5' side of the polymorphic nucleotide(s), or with the 3' to the polymorphic nucleotide(s). A first boundary sequence is contiguous with the 5' side, and a second boundary sequence is contiguous with the 5' side.

The first boundary sequence is the same for each oligonucleotide in a set; the second boundary sequence is also the same for each oligonucleotide in a set, though it generally differs from the first boundary sequence. The first boundary sequence is located at the end of the oligonucleotide that is closest to the solid support when the oligonucleotide is attached to the solid support (also referred to as the "proximal end" of the oligonucleotide), as described below. A linking molecule or molecules can be present, if desired, between the end of the first boundary sequence and the solid support to attach the oligonucleotide to the solid support. The second boundary sequence is at the opposite end of the oligonucleotide from the first boundary sequence (i.e., at the "distal end" of the oligonucleotide).

Between the first and second boundary sequences in the oligonucleotides are nucleic acid markers. A "nucleic acid marker", as used herein, is a nucleic acid that comprises a genetic polymorphism or alteration. The nucleic acid markers are derived from (that is, have essentially the same nucleotide sequence as) a genetic polymorphism or alteration of interest, such as any of the genetic polymorphisms or alterations described above. For example, the nucleic acid markers can contain: repeats of a nucleic acid sequence element, based on a short sequence repeat polymorphism or a VNTR polymorphism; a single nucleotide polymorphism (SNP); nucleic acid containing an allele-specific polymorphism; or nucleic acids for which microdeletions or microinsertions can occur. The nucleic acid marker can also be a "null" marker, containing no nucleic acids: for example, if an allele-specific polymorphism consists of deletion of certain nucleotides, one nucleic acid marker in the set contains the nucleotides, and a second nucleic acid marker in the set contains the deletion (i.e., contains no nucleic acids). Each oligonucleotide in a set contains a different nucleic acid marker.

If the nucleic acid markers are derived from a short sequence repeat polymorphism, each oligonucleotide in a set comprises a nucleic acid marker that contains at least a minimum number (N) of consecutive repeats of a nucleic acid sequence element. The nucleic acid sequence element can be from 2 to 10 bases in length; in one embodiment, the nucleic acid sequence element is 2, 3 or 4 bases in length. The minimum number (N) of consecutive repeats, referred to as the "repeat size", N can be from about 0 to about 40. In one embodiment, N is between about 0 and 20 repeats, inclusive. In another embodiment, N is 0 or 1; in a preferred embodiment, N is 0, as the value N=0 can be used as a control. Alternatively, a higher value of N can also be used, particularly if it is determined empirically that very small N values are not necessary for a particular nucleic acid marker. In a preferred embodiment, the minimum number N is less than or equal to 11 for a short sequence repeat polymorphism. Each nucleic acid marker in the set of oligonucleotides has a different repeat size, where the repeat sizes range from N to N+A, inclusive. The range number (A) is from about 3 to about 60. In one embodiment, A is about 12–18; in another embodiment, A is 15. Thus, for example, if the minimum number (N) of repeats is 0 and the range number (A) of repeats is 15, the set of oligonucleotides includes 16 oligonucleotides, the oligonucleotides comprising nucleic acid markers having a repeat size from 0 to 15, inclusive.

If the nucleic acid markers are derived from a VNTR polymorphism, each oligonucleotide in a set comprises a nucleic acid marker that contains a minimum number N of consecutive repeats of the nucleic acid sequence element, where the nucleic acid sequence element is from about 10 to 60 bases in length. In one embodiment, N is between about 0 and 20 repeats, inclusive. In another embodiment, N is 0 or 1; in a preferred embodiment, N is 0, as the value N=0 can be used as a control. Alternatively, a higher value of N can also be used, particularly if it is determined empirically that very small N values are not necessary for a particular nucleic acid marker. In a preferred embodiment, the minimum number N is less than or equal to 4 for a VNTR polymorphism. As for the nucleic acid markers based on SSR polymorphisms, each nucleic acid marker in this set of oligonucleotides has a different repeat size, where the repeat sizes range from N to N+A, inclusive. The range number (A) is from about 3 to about 20. In one embodiment, A is about 12–18; in another embodiment, A is 15.

If the nucleic acid markers are derived from a single nucleotide polymorphism (SNP), then each oligonucleotide in a set comprises a nucleic acid marker that consists of the polymorphic nucleotide. Each set of oligonucleotides contains four oligonucleotides, each comprising a different nucleic acid marker, each marker having a different nucleotide at the polymorphic nucleotide (i.e., A, T, C or G). In this embodiment, the nucleic acid marker consists solely of the single nucleotide.

If the nucleic acid markers are derived from an allele-specific polymorphism, each oligonucleotide in a set comprises a nucleic acid marker that includes an allele-specific polymorphism. One nucleic acid marker includes the normal (wild-type) allele-specific polymorphism; the rest of the nucleic acid markers each include a mutant allele-specific polymorphism. There are M+1 oligonucleotides in the set, where M is the number of identified mutant allele-specific polymorphisms. The nucleic acid markers may be "null" markers, containing no nucleotides (e.g., if one of the alleles is a deletion).

If the nucleic acid markers are derived from microdeletions or microinsertions, each oligonucleotide in a set comprises a nucleic acid marker that is a fragment of the nucleic acid of interest. The number of nucleic acid markers will depend on the number of different deletions identified. Generally, the nucleic acid markers are about 10 to 30 bases in length; in one embodiment, the fragments are about 20 bases in length. Larger nucleic acid markers can also be used, if desired.

The oligonucleotides can be prepared by conventional methods (see, e.g., *Current Protocols in Molecular Biology* (Ausubel, F. M. et al., eds., containing supplements up through 2000, the teachings of which are hereby incorporated herein by reference; see also, for example, Prodnikov, D. and Mirzabekov, A., *Nucl. Acids. Res.* 24:4535–4542 (1996)). For example, the oligonucleotides can be synthesized as long oligonucleotides (e.g., as continuous oligonucleotides, or as an entire single oligonucleotide), or as short building blocks that are subsequently ligated. The composition and number of the oligonucleotides in the array, as well as the composition of the nucleic acid markers used in the oligonucleotides, depend on what genetic polymorphism is used, as well as on the composition of the nucleic acid of interest. For example, if identification of polymorphism for several SSR loci is desired, several sets of oligonucleotides, where each set of oligonucleotides utilizes a nucleic acid marker containing a different number of nucleic acid sequence elements, can be used.

The oligonucleotides in the set (or sets) are labeled at the distal end of the oligonucleotides. Representative labels include fluorescent agents (dyes or other molecules), chemiluminescent agents, and radionuclides. In one embodiment, the label is a fluorescent label; in another preferred embodiment, the label is a chemiluminescent label. The oligonucleotides can be labeled using standard methods ((see, e.g., *Current Protocols in Molecular Biology* (Ausubel, F. M. et al., eds., containing supplements up through 2000; see also, for example, Prodnikov, D. and Mirzabekov, A., *Nucl. Acids. Res.* 24:4535–4542 (1996)). The label can be attached during preparation of the oligonucleotides, or after completion of oligonucleotide preparation. For example, in one embodiment, the oligonucleotide is labeled by labeling the second boundary sequence before the second boundary sequence is incorporated into the oligonucleotide. Alternatively, the completed oligonucleotide (containing the first boundary sequence, the nucleic acid marker, and the second boundary sequence) can be labeled after it is prepared.

The set (or sets) of oligonucleotides is arranged into an array, such that the position and nucleic acid content of each oligonucleotide in the array is identifiable. In forming an array, the oligonucleotides are immobilized on a solid support (a substrate) or set of solid supports at defined locations (i.e., known positions), so that an array or a set of arrays is prepared. Although the text herein describes, for clarity, "an" oligonucleotide at a defined location, it is intended that each defined location can have a multitude of identical oligonucleotides, and that a multitude of identical oligonucleotides at each defined location are also contemplated by the invention. In addition, redundant defined locations can be used, in which identical oligonucleotides are immobilized at more than one defined location.

The solid support can be a plate or chip of glass, plastic, silicon, or other material. The solid support can also be coated, such as with gold, silver, or silicon dioxide. The coating is between the end of the oligonucleotide and the solid support; such coating may facilitate attachment of oligonucleotides to the surface of the solid support. The oligonucleotides can be attached to the solid support by a linking molecule or molecules; the linking molecule(s) can be any molecule(s) other than nucleic acids which would form part of the oligonucleotide. For example, a specific binding pair, such as biotin and avidin or biotin and streptavidin). Alternatively, the oligonucleotides can be attached by a linking molecule that is a linker "arm", such as a covalently bonded hydrocarbon chain (e.g., a C10–20 chain). The oligonucleotides can also be attached directly to the solid support, such as by epoxide/amine coupling chemistry (see Eggers, M. D. et al., *Advances in DNA Sequencing Technology*, SPIE conference proceedings, Jan. 21, 1993), or any other appropriate means.

If desired, the array can be prepared by an automatic process, such as by photolithographic masking technology (e.g., Jacobs, J. W. and Fodor, S. P., "Combinatorial Chemistry—Applications of Light-directed Chemical Synthesis," in *Trends Biotechnol.* 12(1):19–26 (1994)), or by "miers-jet" reagent application (e.g., Okamoto, T. et al., "Microarray Fabrication with Covalent Attachment of DNA Using Bubble Jet Technology, in *Nat. Biotechnol.* 18(4):438–441 (2000)). In one embodiment of the invention, the oligonucleotides are prepared first, and then attached to the solid support. In another embodiment, the oligonucleotides are prepared (synthesized) directly on the solid support by ligation of individual nucleotides or by ligation of discrete building blocks. For example, a building block that contains the first boundary sequence can be attached to the solid support; subsequently, nucleic acid markers are ligated onto the anchored first boundary sequence. The second boundary sequence is then ligated after the nucleic acid markers.

Each array can also include one or more positive control oligonucleotides (to which the nucleic acid of interest should hybridize), and can also include one or more negative control oligonucleotides (to which the nucleic acid of interest should not hybridize or hybridize completely). Both the positive control oligonucleotides and the negative control nucleotides are labeled at the distal end, as described above. Representative positive control oligonucleotides include an oligonucleotide containing the nucleic acid marker (e.g., repeats of the nucleic acid sequence element), without a first or a second boundary sequence. This oligonucleotide should always give a positive signal (as described below), unless there is exonuclease activity that removes the label, failure in anchoring the oligonucleotides, or failure in labeling. An oligonucleotide that can also serve as a positive control includes the first boundary sequence, but no nucleic acid marker (e.g., no repeats of the nucleic acid sequence element) and no second boundary sequence. This oligonucleotide should always give a positive signal, unless there is a polymorphism in the boundary sequence that would result in it being cleaved (as described below). This would result in the entire array being cleaved and negative. Alternatively, an oligonucleotide containing the second boundary sequence but no nucleic acid marker (e.g., no repeats of the nucleic acid sequence element) and no first boundary sequence can also be used as a positive control. As with an oligonucleotide containing the first boundary sequence (and no nucleic acid marker), this oligonucleotide should also give a positive signal, unless there is a polymorphism in the second boundary sequence. If the nucleic acid markers comprise repeats of nucleic acid sequence elements, an oligonucleotide containing the first boundary sequence plus the maximal number of repeats (N+A), and lacking the second boundary sequence, can also be used as a control. This oligonucleotide has a positive signal if the nucleic acid of interest has more repeats than are designed into the array (i.e., more repeats than N+A); otherwise, it has a negative signal. If the second boundary sequence is "pre-labeled," that is, if the second boundary sequence is labeled prior to its ligation to the repeats of the nucleic acid sequence element during preparation of the oligonucleotides, then the entire unused background region of the solid support of the array (which will not have any label attached) can serve as a negative control, and no separate negative control oligonucleotide is needed. A position on the array that contains no oligonucleotide will have no label attached even if it is subjected to a "labeling" step in the same manner as the set of oligonucleotides within the array, and thus can also be used as a negative control. Any other oligonucleotides that are designed to give either a positive or a negative signal can also be used as controls.

When the nucleic acid markers comprise repeats of a nucleic acid sequence elements, a set of oligonucleotides having N to N+A consecutive repeats of a complementary (second) strand of the nucleic acid sequence element (a "complementary set of oligonucleotides"), can be used as another "control" to confirm the results from the oligonucleotides containing repeats of the first strand of the nucleic acid sequence element. That is, a set of oligonucleotides including oligonucleotides having N to N+A consecutive repeats of a first strand of the nucleic acid sequence element, as well as a set of oligonucleotides having N to N+A consecutive repeats of a second strand of the nucleic acid sequence element, where the second strand is complementary to the first strand of the nucleic acid sequence element, can be used. The oligonucleotides in the complementary set contain the compliments of first and second boundary sequences that are the same as the first and second boundary sequences for the set of oligonucleotides having repeats of the first strand of the nucleic acid sequence element. In this embodiment, the set of oligonucleotides containing repeats of the complementary strand is preferably set forth in a separate array. Using a complementary set is particularly advantageous if the nucleic acid of interest is double-stranded, as the nucleic acid of interest should hybridize to the set of oligonucleotides containing repeats of a first strand of the nucleic acid sequence element, and to the complementary set of oligonucleotides.

In one embodiment, the array includes oligonucleotides containing nucleic acid markers; a negative control; a first positive control that is an oligonucleotide containing the first boundary sequence without a nucleic acid marker and without the second boundary sequence; and a second positive control that is an oligonucleotide containing the second boundary sequence without a nucleic acid marker and without the first boundary sequence. If the nucleic acid marker comprises repeats of a nucleic acid sequence element, the array includes oligonucleotides containing N to N+A repeats of the nucleic acid sequence elements; a negative control; a first positive control that is an oligonucleotide containing the first boundary sequence without repeats of the nucleic acid sequence element and without the second boundary sequence; a second positive control that is an oligonucleotide containing the second boundary sequence without repeats of the nucleic acid sequence element and without the first boundary sequence; and a third control that is an oligonucleotide containing the first boundary sequence and N+A repeats of the nucleic acid sequence element, without the second boundary sequence (this has a negative signal unless the number of repeats in the test sample are equal to, or greater than, N+A).

To perform the assays of the invention, a test sample containing nucleic acid, as described above, is prepared. If the test sample is a biological sample, the nucleic acid in the test sample is isolated from other components of the biological sample using standard methods (see, e.g., *Current Protocols in Molecular Biology* (Ausubel, F. M. et al., eds., containing supplements up through 2000)). If desired, the nucleic acid, or the nucleic acid of interest in the nucleic acid of the sample, can be amplified, such as by using the polymerase chain reaction. If the nucleic acid in the test sample is double-stranded, it is denatured using standard methods to form single-stranded nucleic acid (see, e.g., *Current Protocols in Molecular Biology* (Ausubel, F. M. et al., eds., containing supplements up through 2000). Isolated, denatured (or single-stranded) nucleic acid in a test sample is referred to as a "prepared test sample of nucleic acid". The prepared test sample of nucleic acid comprises nucleic acid having at least one site of genetic polymorphism, as described above.

An array containing a set of oligonucleotides, as described above, is provided. The set of oligonucleotides in the array comprise nucleic acid markers that are derived from the genetic polymorphism that may be present in the prepared test sample of nucleic acid. The array is contacted with the prepared test sample of nucleic acid, such as by placing the prepared test sample on the array. The resulting "contacted array" is maintained under conditions which allow hybridization of nucleic acid in the test sample to the oligonucleotides on the array.

"Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1–2.10.16 and pages 6.3.1–6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1%SDS for 15 min at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used. In a particularly preferred embodiment, the hybridization conditions for specific hybridization are high stringency. In another embodiment, the contacted array is maintained under conditions that include low stringency conditions.

Under such conditions, if the prepared test sample contains nucleic acid that comprises the nucleic acid marker in one of the oligonucleotides in the array, the nucleic acid hybridizes completely with that oligonucleotide, resulting in a "completely hybridized oligonucleotide". For example, if the nucleic acid of interest contains nucleic acid that comprises the same number of repeats of the same nucleic acid sequence element as one of the oligonucleotides in the array, the nucleic acid hybridizes completely with that oligonucleotide. If the nucleic acid of interest contains nucleic acid that is slightly different from the nucleic acid marker, incomplete hybridization between the nucleic acid and the oligonucleotide occurs (resulting in an "incompletely hybridized oligonucleotide"). For example, if the nucleic acid of interest comprises a nucleic acid that has a different number of repeats of a nucleic acid sequence element than the number of repeats in the nucleic acid marker, or that has a single nucleotide difference from the nucleic acid marker, incomplete hybridization occurs, resulting in an "incompletely hybridized oligonucleotide". Incomplete hybridization results in portions or "bubbles" of single-stranded nucleic acid. Hybridization of nucleic acid in the test sample to oligonucleotides on the array results in a "hybridized array" which generally contains both completely hybridized oligonucleotides and incompletely hybridized oligonucleotides.

The hybridized array is then subjected to a cleavage agent, such as a single-strand cleavage agent, forming a "cleaved array". For example, the hybridized array can exposed to a single stranded endonuclease, such as mung bean nuclease, S1 nuclease, or other nuclease. Alternatively, a chemical mismatch cleavage system, such as that described by Cotton, R. G. H. et al. (Cotton, R. G. H. et al., *Proc. Natl. Acad. Sci.* 85:4397–4401 (1988)) or Meyers, R. M. et al., (Meyers, R.

M. et al., *Science* 230:1242–1246 (1985)) can be used. Single strand cleavage results in cleavage of incompletely hybridized oligonucleotides, because the single strand cleavage agent cleaves the single-stranded "bubbles" of nucleic acid that appear on the incompletely hybridized oligonucleotides. Cleavage of the incompletely hybridized oligonucleotides results in cleavage products that comprise the portion of the oligonucleotide that is distal from the point of incomplete hybridization (that is, the portion of the oligonucleotide that is distal from the single-stranded bubble of nucleic acid). This distal portion of the oligonucleotide includes the label that is at the distal end of the oligonucleotide. The completely hybridized oligonucleotides are not cleaved, and thus the label remains indirectly bound to the substrate. The completely hybridized oligonucleotides that retain label are deemed to have a "positive" signal; the incompletely hybridized oligonucleotides, from which label has been cleaved, have a "negative" signal. Cleavage of the incompletely hybridized oligonucleotides results in cleavage products that comprise the portion of the oligonucleotide that is either proximal or distal from the point of incomplete hybridization (that is, the portion of the oligonucleotide that is distal from the single-stranded bubble of nucleic acid). This portion of the oligonucleotide includes the label that is at the distal end of the oligonucleotide. The completely hybridized oligonucleotides are not cleaved, and thus the label remains indirectly bound to the substrate. As above, the completely hybridized oligonucleotides that retain label are deemed to have a "positive" signal; the incompletely hybridized oligonucleotides, from which label has been cleaved, have a "negative" signal.

Each test sample generates a particular pattern of positive and negative signals on the cleaved array, based on the positions of the completely hybridized oligonucleotides and the positions of the incompletely hybridized oligonucleotides.

The cleaved array is washed as necessary to remove cleavage products from the cleaved array. Generally, a buffered solution can be used as a washing solution. The washing solution can be used to facilitate cessation of the action ("quenching") of the cleavage agent. For example, if an enzyme is used as a cleavage agent, the washing solution can contain EDTA to inactivate the enzyme; in another embodiment, if an acidic chemical cleavage agent is used, the washing solution can be basic. In one embodiment, cleavage in a chemical mismatch cleavage system is performed with Piperidine after treatment with hydroxylamine or osmium tetroxide, followed by precipitation with ethanol and washing with 70% ethanol. Alternatively, in another embodiment, 0.5% SDS can be used for washing.

The pattern of positive and negative signals on the washed, cleaved array can be observed, assessed and/or analyzed using an instrument that is appropriate to detect the label. For example, if the label on the oligonucleotides was a fluorescent label, a fluorescent microscope can be used. Alternatively, a CCD camera, or other "reader" can be used, as can human vision. A computer image analysis system can also be used to analyze and interpret the label pattern.

The pattern of positive and negative signals on the washed, cleaved array is determined by the nucleic acid markers that were used in the set of oligonucleotides on the array. For example, if the nucleic acid markers contain repeats of a nucleic acid sequence element, completely hybridized oligonucleotides (having a positive signal) are those oligonucleotides that comprise a nucleic acid marker containing the same number of repeats as are present in nucleic acid of the test sample; incompletely hybridized oligonucleotides (having a negative signal) are those oligonucleotides that comprise a nucleic acid marker containing a different number of repeats as are present in nucleic acid of the test sample. If the nucleic acid markers contain single nucleotide polymorphisms, only that oligonucleotide comprising a nucleic acid marker having the same nucleotide polymorphism as the nucleic acid in the test sample completely hybridizes and has a positive signal. The three other oligonucleotides in the set (comprising nucleic acid markers having a different nucleotide at the single nucleotide polymorphism) have a negative signal. If the nucleic acid markers contain allele-specific polymorphisms, those oligonucleotides comprising a nucleic acid marker having the same allele-specific polymorphism as the nucleic acid in the test sample completely hybridize and have a positive signal. If only mutant allele-specific polymorphisms are present in the nucleic acid of the test sample, the oligonucleotide comprising a nucleic acid marker containing the wild-type (normal) allele-specific polymorphism has a negative signal. If the nucleic acid markers contain fragments of the nucleic acid of interest, then those oligonucleotides that comprise nucleic acid markers containing fragments of the nucleic acid of interest that are present in the nucleic acid of the test sample have a positive signal; if a microdeletion exists in the nucleic acid of the test sample, the oligonucleotide(s) that comprises a nucleic acid marker containing the fragment of nucleic acid that is deleted has a negative signal, because the signal is cleaved from those oligonucleotides that cannot hybridize (the hybridizing fragment is missing from the test sample).

Because each test sample yields a particular positive and negative signal pattern on the array, the signal pattern of many different samples of nucleic acid of interest can be quickly and easily compared. Use of arrays that are bound to a solid support allows automated high-density array- or "DNA chip"-based analyses. Furthermore, because the nucleic acid markers can provide a high degree of polymorphism (e.g., SSR polymorphisms and VNTR polymorphisms), or a high density of polymorphisms (e.g., SNP polymorphisms), more distinctive label patterns can be yielded for each test sample. In addition, disease-associated polymorphisms and alterations (e.g., allele-specific polymorphisms, microdeletions, microinsertions) can be quickly identified.

Although the above discussion describes assays that identify particular genetic polymorphisms in a test sample of nucleic acid, the assays can also be used for generalized mutation screening or analysis when the nucleic acid sequence of the nucleic acid of interest is known. The set of oligonucleotides for use in identifying an unknown mutation is similar to the set of oligonucleotides used in identifying a microdeletion: each oligonucleotide comprises a nucleic acid marker that contains a fragment of the nucleic acid of interest. For example, 20,000 base pairs of DNA can be evaluated for polymorphism with an array of oligonucleotides comprising 1,000 twenty-base nucleic acid markers. The positive signals indicate those oligonucleotides that comprise a nucleic acid marker that hybridizes to wild-type (normal) nucleic acid from the test sample; the negative signals indicate those oligonucleotides which comprise a nucleic acid marker that incompletely hybridizes to nucleic acid from the test sample. If negative signals appear, indicating incomplete hybridization, then the nucleic acid which incompletely hybridizes comprises an alteration (e.g., a mutation). The location of the mutation can therefore be narrowed down to nucleic acid hybridizing to a particular nucleic acid marker (e.g., a 20 base pair stretch of DNA).

The 20 base pairs of nucleic acid from the test sample can be easily sequenced, or evaluated on another array with single base resolution to identify the specific polymorphism.

Although the discussion above has been directed towards assays in which the set of oligonucleotides is attached in an array to a solid support, the methods described herein can also be used by attaching the set of oligonucleotides to a different type of solid support, not in an array. For example, each oligonucleotide in the set is attached to a solid support particle (e.g., a polystyrene bead or microsphere); the solid support particles are labeled in a manner that allows identification of the individual particles (and thereby, allows identification of the oligonucleotide and its composition attached to the particle). Representative labeling systems include the LabMAP (Laboratory Multiple Analyte Profiling) system, from Luminex Corporation (Austin, Tex.). The assays are run as described above, except that the reactions are performed, for example, in solution in lieu of on an array. The pattern of negative and positive signals on the individually identifiable particles can be interpreted in the same manner as the pattern of negative and positive signals on a washed, cleaved array as described above.

For example, in one embodiment, a set of oligonucleotides as described above is provided, where the oligonucleotides are attached to solid support particles which are labeled to allow identification of the oligonucleotide attached to each particle; the set of oligonucleotides is contacted with a prepared test sample of nucleic acid, as described above, and maintained under conditions which allow hybridization of nucleic acid in the test sample to the oligonucleotides of the array, to form a hybridized oligonucleotide set. The hybridized oligonucleotide set is subjected to a cleavage agent that cleaves incompletely hybridized oligonucleotides but does not cleave completely hybridized oligonucleotides, as described above, and the resultant cleaved oligonucleotide set is washed to remove cleavage products. The negative and positive signals on the washed, cleaved oligonucleotide set, are then assessed, such as by determining which particles (and thus, which of the oligonucleotides of the set) have negative signals and which have positive signals.

The following Exemplification is offered for the purpose of illustrating the present invention and are not to be construed to limit the scope of this invention. The teachings of all references cited are hereby incorporated herein in their entirety.

Exemplification

Use of Methods for Detecting Mutations Associated with Cystic Fibrosis

Figure 1A:
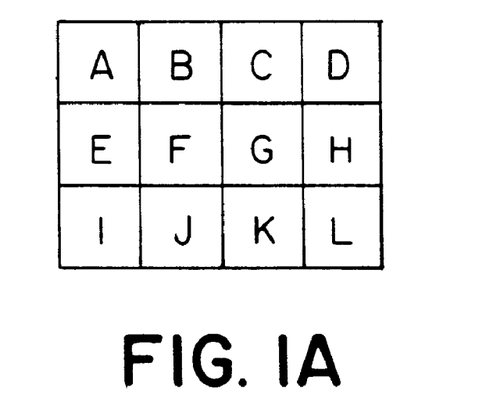
FIG. 1A is a representation of an oligonucleotide array for identification of 6 mutations in the CFTR gene associated with cystic fibrosis.
Figure 1B:
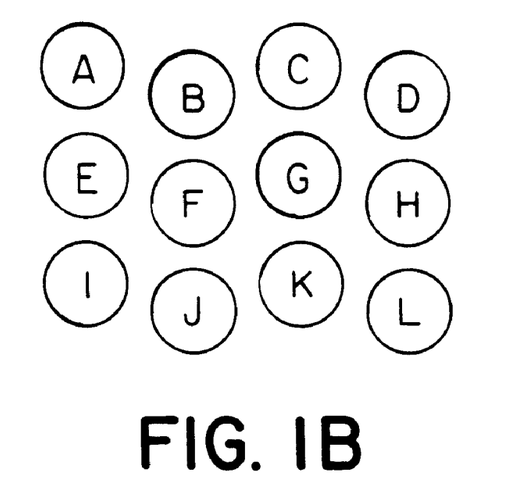
FIG. 1B is a representation of a group of solid phase particles for identification of 6 mutations in the CFTR gene associated with cystic fibrosis.
Figure 1C:
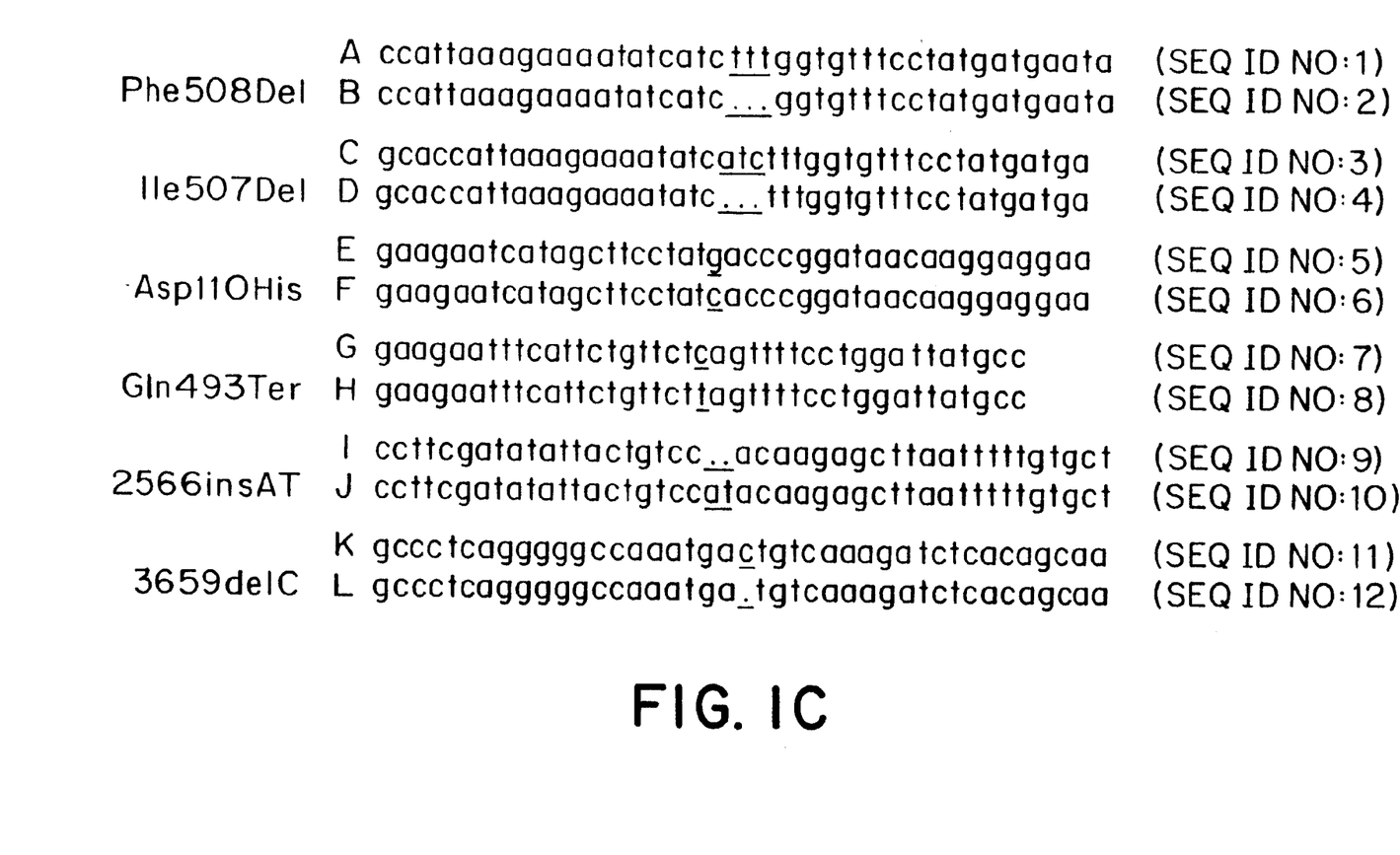
FIG. 1C depicts six mutations (Phe508Del; Ile507Del; Asp110His; Gln493Ter;2566insAT; and 3659delC, respectively) in the gene CFTR, that are associated with cystic fibrosis. The nucleic acid markers for the native (non-mutant) are set forth as A (SEQ ID NO: 1), C (SEQ ID NO: 3), E (SEQ ID NO: 5), G (SEQ ID NO: 7), I (SEQ ID NO: 9), and K (SEQ ID NO: 11); the mutations are set forth as B (SEQ ID NO: 2), D (SEQ ID NO: 4), F (SEQ ID NO: 6), H (SEQ ID NO: 8), J (SEQ ID NO: 10), and L (SEQ ID NO: 12).

Oligonucleotide arrays are prepared as described herein. A representative array, depicting the nucleic acid markers for each oligonucleotide, is shown in FIG. 1A. Alternatively, solid support particles can be used, as shown in FIG. 1B. Six mutations in the gene, CFTR, that are associated with cystic fibrosis are set forth, as are the native (non-mutant) counterparts to the mutations (FIG. 1C). Mutations are identified in FIGS. 1A–C as B, D, F, H, J, and L (phe508Del; Ile507Del; Asp110His; Gln493Ter;2566insAT; and 3659delC, respectively); the native counterparts are identified as A, C, E, G, I, and K. The oligonucleotide at each position (e.g., "A", "B", etc.) shown in FIG. 1A, or on each solid support particle shown in FIG. 1B, comprises the nucleic acid marker shown in FIG. 1C.

Test samples (e.g., genomic DNA from a test individual, or nucleic acids comprising the CFTR gene from a test individual, such as PCR products of genomic DNA) are prepared and contacted with the array (or the group of solid support particles). Hybridization is allowed to occur; a cleavage agent is applied; the cleaved array is washed; and the pattern of signals is assessed. A positive signal indicates that nucleic acid in the sample hybridizes completely to the nucleic acid marker of that oligonucleotide. A negative signal indicates that nucleic acid in the sample hybridizes incompletely to the nucleic acid marker of that oligonucleotide. Representative results are shown in FIGS. 2A and 2B and in FIGS. 3A and 3B.

Figure 2A:
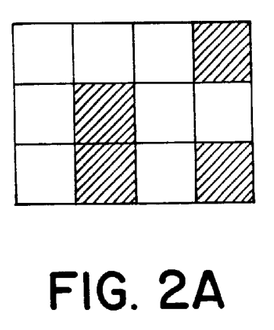
FIGS. 2A (array) and 2B (solid phase particles) represent the pattern of negative and positive signals if the test sample is from an individual that is heterozygous for the Phe508Del and Gln493Ter mutations.
Figure 2B:
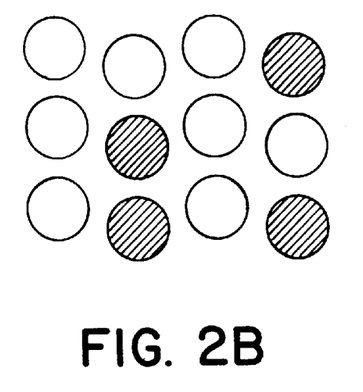

FIGS. 2A (array) and 2B (solid phase particles) represent the pattern of negative and positive signals if the test sample is from an individual that is heterozygous for the Phe508Del and Gln493Ter mutations (i.e., alleles A, B, C, E, G, H, I and K not cleaved since they are present in the patient; D, F, J and L cleaved since they are not present in the patient.

Figure 3A:
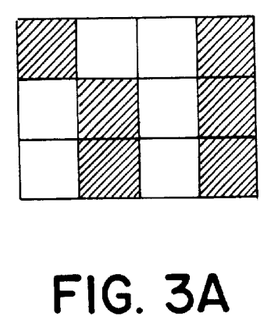
FIGS. 3A (array) and 3B (solid phase particles) represent the pattern of negative and positive signals if the test sample is from an individual that is homozygous for the Phe508Del mutation.
Figure 3B:
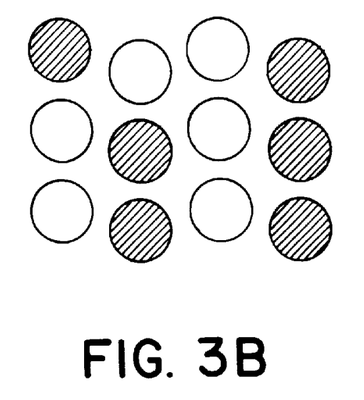

FIGS. 3A (array) and 3B (solid phase particles) represent the pattern of negative and positive signals if the test sample is from an individual that is homozygous for the Phe508Del mutation (i.e., alleles B, C, E, G, I and K not cleaved since they are not present in the patient; A, D, F, H, J and L cleaved since they are not present in the patient).

Equivalents

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An assay for analyzing a test sample comprising nucleic acid, comprising the steps of:
   a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a nucleic acid marker between the first and second boundary sequences, and a label at the distal end of the oligonucleotide; and wherein each oligonucleotide in the set of oligonucleotides has a different nucleic acid marker;
   b) contacting the array with a prepared test sample of nucleic acid, thereby forming a contacted array;
   c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;
   d) subjecting the hybridized array to a cleavage agent, wherein the cleavage agent cleaves incompletely hybridized oligonucleotides but does not cleave completely hybridized oligonucleotides, thereby forming a cleaved array and cleavage products;
   e) washing the cleaved array to remove cleavage products from the cleaved array;
   f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

2. The assay of claim 1, wherein each different nucleic acid marker contains a minimum number N of consecutive repeats of a nucleic acid sequence element, and wherein each different nucleic acid marker has a different number of consecutive repeats of the nucleic acid sequence element, the number ranging from N to N+A, inclusive.

3. The assay of claim 1, wherein each different nucleic acid marker contains a polymorphic nucleotide.

4. The assay of claim 1, wherein each different nucleic acid marker contains an allele-specific polymorphism.

5. The assay of claim 1, wherein each different nucleic acid marker contains a nucleic acid of interest.

6. The assay of claim 5, wherein each nucleic acid of interest contains from 10 to 30 bases.

7. The assay of claim 1, wherein the label at the distal end of the oligonucleotide is selected from the group consisting of: a fluorescent agent, a chemiluminescent agent, and a radionuclide.

8. The assay of claim 1, wherein the array further comprises a positive control oligonucleotide.

9. The assay of claim 8, wherein the positive control oligonucleotide contains a nucleic acid marker and a label at the distal end of the oligonucleotide, and does not include a first boundary sequence or a second boundary sequence.

10. The assay of claim 8, wherein the positive control oligonucleotide contains a first boundary sequence and the label at a distal end of the oligonucleotide, and does not include a nucleic acid marker or a second boundary sequence.

11. The assay of claim 8, wherein the positive control oligonucleotide contains a second boundary sequence and the label at a distal end of the oligonucleotide, and does not include a nucleic acid marker or a first boundary sequence.

12. The assay of claim 1, wherein the array further comprises a negative control oligonucleotide.

13. The method of claim 1, wherein the test sample comprising nucleic acid comprises genomic DNA comprising part of the genome of an individual.

14. The method of claim 1, wherein the test sample comprising nucleic acid comprises genomic DNA comprising the entire genome of an individual.

15. An assay for analyzing a test sample comprising nucleic acid, comprising the steps of:
   a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a minimum number N of consecutive repeats of a nucleic acid sequence element between the first and second boundary sequences, and a label at the distal end of the oligonucleotide; and wherein each oligonucleotide in the set of oligonucleotides has a different number of consecutive repeats of the nucleic acid sequence element, the number ranging from N to N+A, inclusive;

b) contacting the array with a prepared test sample of nucleic acid, thereby forming a contacted array;

c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;

d) subjecting the hybridized array to a cleavage agent, wherein the cleavage agent cleaves incompletely hybridized oligonucleotides but does not cleave completely hybridized oligonucleotides, thereby forming a cleaved array and cleavage products;

e) washing the cleaved array to remove cleavage products from the cleaved array;

f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

16. The assay of claim 15, wherein N is from 0 to 40.

17. The assay of claim 16, wherein N is from 0 to 20.

18. The assay of claim 15, wherein A is from 1 to 60.

19. The assay of claim 18, wherein A is from 12 to 18.

20. The assay of claim 15, wherein the nucleic acid sequence element is from 1 to 12 bases in length.

21. The assay of claim 20, wherein the nucleic acid sequence element is from 2 to 4 bases in length.

22. The assay of claim 15, wherein the label at the distal end of the oligonucleotide is selected from the group consisting of: a fluorescent agent, a chemiluminescent agent, and a radionuclide.

23. The assay of claim 15, wherein the array further comprises a positive control oligonucleotide.

24. The assay of claim 23, wherein the positive control oligonucleotide contains a number of consecutive repeats of the nucleic acid sequence element and the label at a distal end of the oligonucleotide, and does not include the first boundary sequence or the second boundary sequence.

25. The assay of claim 23, wherein the positive control oligonucleotide contains the first boundary sequence and the label at a distal end of the oligonucleotide, and does not include any consecutive repeats of the nucleic acid sequence element or the second boundary sequence.

26. The assay of claim 23, wherein the positive control oligonucleotide contains the second boundary sequence and the label at a distal end of the oligonucleotide, and does not include any consecutive repeats of the nucleic acid sequence element or the first boundary sequence.

27. The assay of claim 15, wherein the array further comprises a negative control oligonucleotide.

28. The method of claim 15, wherein the test sample of nucleic acid comprises genomic DNA comprising part of the genome of an individual.

29. The method of claim 15, wherein the test sample of nucleic acid comprises genomic DNA comprising the entire genome of an individual.

30. An assay for analyzing a test sample comprising nucleic acid, comprising the steps of:

a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a minimum number N of consecutive repeats of a nucleic acid sequence element between the first and second boundary sequences, and a fluorescent label at the distal end of the oligonucleotide; and wherein each oligonucleotide in the set of oligonucleotides has a different number of consecutive repeats of the nucleic acid sequence element, the number ranging from 0 to 15, inclusive;

b) contacting the array with a prepared test sample of nucleic acid, thereby forming a contacted array;

c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;

d) subjecting the hybridized array to a cleavage agent, wherein the cleavage agent cleaves incompletely hybridized oligonucleotides but does not cleave completely hybridized oligonucleotides, thereby forming a cleaved array and cleavage products;

e) washing the cleaved array to remove cleavage products from the cleaved array;

f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

31. An assay for analyzing a test sample comprising nucleic acid, comprising the steps of:

a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a nucleic acid marker between the first and second boundary sequences, and a label at the distal end of the oligonucleotide; wherein each nucleic acid marker contains a single nucleotide polymorphism; and wherein each oligonucleotide in the set of oligonucleotides has a different nucleotide at the single nucleotide polymorphism;

b) contacting the array with a prepared test sample of nucleic acid, thereby forming a contacted array;

c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;

d) subjecting the hybridized array to a cleavage agent, wherein the cleavage agent cleaves incompletely hybridized oligonucleotides but does not cleave completely hybridized oligonucleotides, thereby forming a cleaved array and cleavage products;

e) washing the cleaved array to remove cleavage products from the cleaved array;

f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

32. An assay for analyzing a test sample comprising nucleic acid, comprising the steps of:
 a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a nucleic acid marker between the first and second boundary sequences, and a label at the distal end of the oligonucleotide; wherein each nucleic acid marker contains an allele-specific polymorphism; and wherein each oligonucleotide in the set of oligonucleotides has a different allele-specific polymorphism;
 b) contacting the array with a prepared test sample of nucleic acid, thereby forming a contacted array;
 c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;
 d) subjecting the hybridized array to a cleavage agent, wherein the cleavage agent cleaves incompletely hybridized oligonucleotides but does not cleave completely hybridized oligonucleotides, thereby forming a cleaved array and cleavage products;
 e) washing the cleaved array to remove cleavage products from the cleaved array;
 f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

33. An assay for analyzing a test sample comprising nucleic acid, comprising the steps of:
 a) providing an array comprising a set of oligonucleotides attached to a solid support at identifiable locations, wherein each oligonucleotide in the set comprises a first boundary sequence at a proximal end of the oligonucleotide, a second boundary sequence at a distal end of the oligonucleotide, a nucleic acid marker between the first and second boundary sequences, and a label at the distal end of the oligonucleotide; wherein each nucleic acid marker contains a fragment of a nucleic acid of interest;
 b) contacting the array with a prepared test sample of nucleic acid, thereby forming a contacted array;
 c) maintaining the contacted array under conditions which allow hybridization of nucleic acid in the test sample to the oligonucleotides of the array, thereby forming a hybridized array comprising incompletely hybridized oligonucleotides and completely hybridized oligonucleotides;
 d) subjecting the hybridized array to a cleavage agent, wherein the cleavage agent cleaves incompletely hybridized oligonucleotides but does not cleave completely hybridized oligonucleotides, thereby forming a cleaved array and cleavage products;
 e) washing the cleaved array to remove cleavage products from the cleaved array;
 f) assessing a pattern of negative and positive signals on the washed, cleaved array, wherein a negative signal corresponds to an incompletely hybridized oligonucleotide that was cleaved by the cleavage agent, and a positive signal corresponds to an oligonucleotide that was not cleaved by the cleavage agent.

34. An assay for analyzing a test sample comprising nucleic acid, comprising the steps of:
 a) providing a set of oligonucleotides attached to labeled solid support particles, wherein each oligonucleotide in the set comprises a first boundary sequence at a proximal end of the oligonucleotide, a second boundary sequence at a distal end of the oligonucleotide, a nucleic acid marker between the first and second boundary sequences, and a label at the distal end of the oligonucleotide; wherein each oligonucleotide in the set of oligonucleotides has a different nucleic acid marker; and wherein the solid support particles are labeled to allow identification of the oligonucleotide attached to each particle;
 b) contacting the set of oligonucleotides with a prepared test sample of nucleic acid, thereby forming a contacted oligonucleotide set;
 c) maintaining the contacted oligonucleotide set under conditions which allow hybridization of nucleic acid in the test sample to the oligonucleotides of the array, thereby forming a hybridized oligonucleotide set comprising incompletely hybridized oligonucleotides and completely hybridized oligonucleotides;
 d) subjecting the hybridized oligonucleotide set to a cleavage agent, wherein the cleavage agent cleaves incompletely hybridized oligonucleotides but does not cleave completely hybridized oligonucleotides, thereby forming a cleaved oligonucleotide set and cleavage products;
 e) washing the cleaved oligonucleotide set to remove cleavage products from the cleaved oligonucleotide set;
 f) assessing negative and positive signals on the washed, cleaved oligonucleotide set, wherein a negative signal corresponds to an incompletely hybridized oligonucleotide that was cleaved by the cleavage agent, and a positive signal corresponds to an oligonucleotide that was not cleaved by the cleavage agent.

* * * * *